(12) United States Patent
Randell et al.

(10) Patent No.: US 7,526,330 B1
(45) Date of Patent: Apr. 28, 2009

(54) MAGNETIC RESONANCE SCANNING APPARATUS

(75) Inventors: Christopher Paul Randell, Guildford (GB); Navjeet Chhina, Leamington Spa (GB)

(73) Assignee: Pulseteq Limited, Guildford, Surrey (GB)

( * ) Notice: Subject to any disclaimer, the term of this patent is extended or adjusted under 35 U.S.C. 154(b) by 828 days.

(21) Appl. No.: 10/885,052

(22) Filed: Jul. 6, 2004

(51) Int. Cl.
*A61B 5/05* (2006.01)

(52) U.S. Cl. ............... 600/421; 600/422; 600/418; 324/309; 324/318

(58) Field of Classification Search ............ 600/421, 600/422, 415, 411, 410, 418; 324/318, 320, 324/322, 308, 309
See application file for complete search history.

(56) References Cited

U.S. PATENT DOCUMENTS

| | | | | |
|---|---|---|---|---|
| 4,804,261 A | * | 2/1989 | Kirschen | 351/158 |
| 5,085,219 A | * | 2/1992 | Ortendahl et al. | 600/422 |
| 5,274,332 A | * | 12/1993 | Jaskolski et al. | 324/318 |
| 5,388,580 A | * | 2/1995 | Sullivan et al. | 600/421 |
| 5,435,302 A | * | 7/1995 | Lenkinski et al. | 600/422 |
| 6,138,302 A | * | 10/2000 | Sashin et al. | 5/600 |
| 6,241,669 B1 | * | 6/2001 | Furuta et al. | 600/422 |
| 6,463,316 B1 | * | 10/2002 | Brungart | 600/410 |
| 6,577,888 B1 | * | 6/2003 | Chan et al. | 600/422 |
| 6,784,665 B1 | * | 8/2004 | Chan et al. | 324/318 |
| 6,980,002 B1 | * | 12/2005 | Petropoulos et al. | 324/318 |
| 2004/0030238 A1 | * | 2/2004 | Vaughan | 600/418 |
| 2005/0107686 A1 | * | 5/2005 | Chan et al. | 600/422 |

* cited by examiner

*Primary Examiner*—Eric F Winakur
*Assistant Examiner*—Katherine L Fernandez
(74) *Attorney, Agent, or Firm*—Richard M. Goldberg (57) ABSTRACT

Magnetic resonance scanning apparatus for imaging parts of a human head includes RF coils configured to receive an RF signal including upper and lower pairs of RF coils; a lower supporting structure; and an upper part. The lower supporting structure has an upper wall providing support for the back of a human head, with the lower pair of RF coils rigidly mounted therein. The upper part has a rigid structure supporting the upper pair of RF coils. Each RF coil is located on a concave surface curving circumferentially and longitudinally around a human head located within the apparatus. Each of the upper pair of RF coils has an outer boundary following a contour between the eyes, around the bridge of a nose and below a respective eye located within the apparatus to allow the nose to extend between the upper pair of RF coils.

20 Claims, 11 Drawing Sheets

MAGNETIC RESONANCE SCANNING APPARATUS

BACKGROUND OF THE INVENTION

1. Field of the Invention

The present invention relates to magnetic resonance scanning apparatus for imaging parts of a human head comprising a plurality of RF coils configured to receive an RF signal. In particular, the invention relates to neurological imaging apparatus.

2. Description of the Related Art

In a magnetic resonance imaging system for imaging parts of a human head, it is known to have RF (radio frequency) transmitting coils which transmit RF pulses to the head, and separate RF coils configured to receive the consequently emitted RF signals from the various tissues of the head.

Typically, the receiving RF coils form an array of small sized coils surrounding the head of a human subject. In recent years, a technique referred to as parallel imaging has been developed which allows each coil in an array to provide a different signal, and thereby provide further spatial information and reduce required scanning times. Such coil arrays are configured on a rigid circular former that surrounds the head giving reasonable clearance to allow the head good access, and therefore spaced away from the head, typically on a diameter of 27 cm or more, or they are based on dome shaped rigid structures that cover the top of the head but not below the eyes. One continuing problem with such RF receiving coils is the less than optimal signal to noise ratios of the signals they produce.

A further problem with existing RF receiving coils is the claustrophobic effect they can have on the human subject, due to their appearance over their face.

Yet another problem with such receiving coil arrays is that they generally rely on the human subject to keep their head stationary during the several minutes it takes to perform the scan.

BRIEF SUMMARY OF THE INVENTION

According to a first aspect of the present invention there is provided Magnetic resonance scanning apparatus for imaging parts of a human head comprising: a plurality of RF coils configured to receive an RF signal including a lower pair of RF coils and an upper pair of RF coils; a lower supporting structure; and an upper part, wherein said lower supporting structure has an upper wall configured to provide support for the back of a human head said lower pair of RF coils is rigidly mounted within the lower portion adjacent the upper wall, said upper part has a rigid structure supporting said upper pair of RF coils, each of said RF coils are located on a concave surface configured to curve circumferentially around a human head and longitudinally around a human head when located within the apparatus, and each of said upper pair of RF coils has an outer boundary configured to follow a contour between the eyes around the bridge of a nose and below a respective eye of a human head when located within the apparatus to allow the nose to extend between said upper pair of RF coils, whereby a close spacing is provided between the RF coils and an upper part of a head including a part which is adjacent to the eyes.

In a particular embodiment the coils are configured to provide a non-uniform radio frequency field such that said coils are useable in a parallel imaging system. In a particular embodiment, each of said plurality of coils is configured to be de-coupled from the other coils such that said coils are useable in a parallel imaging system.

In a particular embodiment the apparatus further comprises goggles attachable to the lower part and configured to press on the face of a person to resist the movement of their head. In a particular embodiment, the apparatus further comprises ear covers attached to the lower part or the upper part, said covers being configured to provide a force on the sides of a person's head to resist movement of the head.

WRITTEN DESCRIPTION OF THE BEST MODE FOR CARRYING OUT THE INVENTION

FIG. 1

Figure 1:
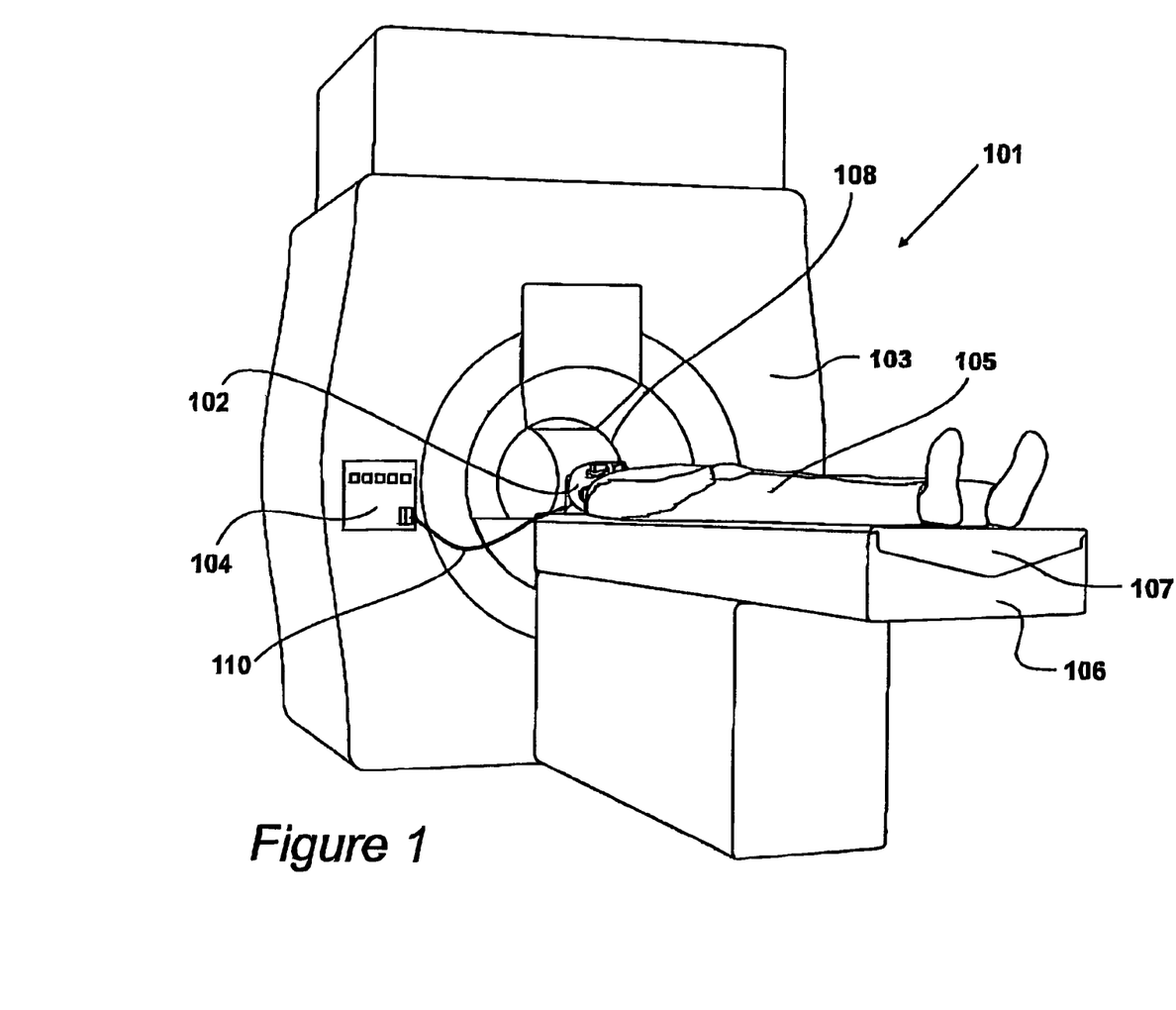
FIG. 1 shows magnetic resonance imaging equipment 101 which includes apparatus 102 embodying the present invention.

Magnetic resonance Imaging (MRI) equipment 101 is shown in FIG. 1 which includes apparatus 102 embodying the present invention. The magnetic resonance imaging equipment 101 has a main unit 103 containing the main magnet, gradient coils and RF (radio frequency) excitation coils, as are known in the art.

During operation, the main magnet produces a constant very high intensity uniform magnetic field (typically 0.5 to 3.0 Tesla) which causes alignment of hydrogen nuclei in the body part to be scanned. Under the control of a scanner control unit, he transmitting RF coils are arranged to produce radio frequency pulses which cause the aligned hydrogen nuclei to process. After the RF pulse ends, the precessing nuclei cause an RF signal to be detected by RF receiving coils. The gradient magnetic fields are switched both during and after the RF pulse according to one of many known MR imaging protocols. These control both the region from which the MR signal is generated and the spatial encoding in the MR signal that is required to reconstruct the MR image.

The apparatus 102 contains RF receiving coils which are used to receive the signals emitted by the precessing nuclei, and pre-amplifiers which provide amplified signals to a signal processing unit 104 via cable 110. The signal processing unit 104 uses an appropriate image reconstruction algorithm to process the signals derived from each of the coils in the apparatus 102 to produce two or three-dimensional maps and/or images of the body part being scanned.

A person 105 is shown in FIG. 1 on a bed 106 awaiting a scan of their head. The bed has a sliding portion 107 on which the person lays, which is driven along to bring the person's head into the center of the bore 108 of the main magnet. The scanning process may then begin.

Many of the various types of MR scans and MR studies can take many minutes (in some cases 10 minutes or more). During this time, the person must keep their head still, otherwise the scan may be made useless and need to be repeated.

The bore is itself sufficiently narrow to cause a feeling of claustrophobia in some patients. In addition, while the equipment 101 performs its scan, the person 105 is subjected to a loud hammering noise caused by vibration of the gradient magnets as they pulse within the main magnetic field. This also can be disconcerting to some patients.

FIG. 2

Figure 2:
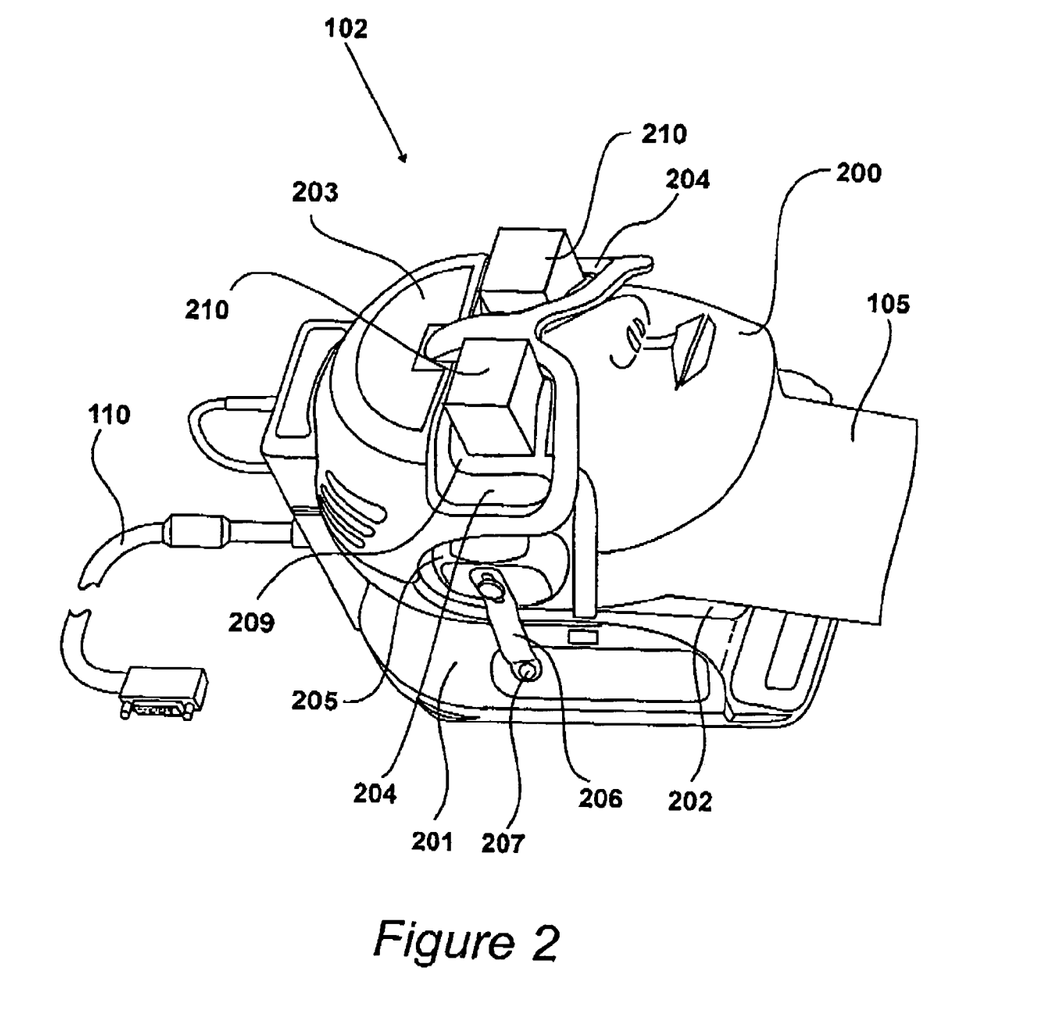
FIG. 2 shows a detailed view of the receiving coil apparatus 102 and the head 200 of the person 105.

A detailed view of the receiving coil apparatus 102 and the head 200 of the person 105 is shown in FIG. 2. The cable 110 is shown with a central section removed to simplify the illustration.

The apparatus comprises a lower part, i.e. a base, which has an under-surface (not shown) configured to provide a stable fit onto the bed 106, and an upper surface 202 having a concave shape configured to provide support for a substantial portion of the back of a head 200. Specifically, the upper surface 202 curves circumferentially upwards around the head from the back to the sides of the head, and also curves upwards longitudinally from the back to the top of the head. The upper surface 202 is provided with a shaped cushion, or alternatively a vacuum bean-bag device, to assist the stabilization of the person's head.

The apparatus 102 also has an upper part 203 which is attached to the lower part 201 to surround the head 200. The lower and upper parts of the apparatus each contain a number of rigidly supported RF receiving coils that are closely spaced from the head 200. The lower part 201 and upper part 203 are each shaped to fit around a person's ear and to leave space for ear covers such as earphones or ear protectors.

The upper part 203 has an open structure such that it defines apertures 204 in front of the person's eyes to allow them to see out from the apparatus. Consequently, a user may wear goggles providing a visual display or, if goggles are not worn, the openness of the upper part assists in alleviating the feeling of claustrophobia which may be experienced by the person.

As shown in FIG. 2 the apparatus 102 includes ear covers 205, in the form of pair of earphones attached to the lower part 201 by brackets 206. The brackets 206 are made of a stiff material which has a degree of resilience, such as a rigid plastics material. Consequently, the earphones 205 are arranged to press against the sides of the head and thereby resist movement of the head.

The lower end of each bracket 206 is anchored to the lower part 201 by a threaded fixing 207, while the upper end is attached to the respective earphone. A slot in the bracket, where the earphone is attached, provides a means of adjusting the distance between the lower part 201 and the earphone 205. In an alternative embodiment, the bracket is telescopic to provide the means of adjustment.

In the present embodiment the ear covers 205 are earphones and therefore may provide the wearer with audio stimulation, but in an alternative embodiment the ear covers are simply ear protectors to reduce the degree of noise for the wearer.

In yet another alternative embodiment, the ear covers themselves contain an RF receiving coil extending around their periphery. These coils are used when the inner ear is to be scanned, and may be used in isolation of, or in parallel with, the RF coils of the upper and lower parts (203 and 201).

The apparatus 102 also includes goggles 209 which provide the person 105 with a visual stimulation. For example, the person 105 may watch, and listen to, a video recording by means of goggles 209 and earphones 205. The goggles have housings 210 which extend through the aperture 204 in the upper part 203. The housings 210 contain angled mirrors by which the person 105 is able to look backwards through the bore 108 of the main unit 103 to a visual display unit (not shown), or other screen, displaying video images. In an alternative embodiment, the housings 210 each contain a small liquid crystal display (LCD) unit and lenses allowing the person 105 to view video images presented on the LCD.

FIG. 3

Figure 3:
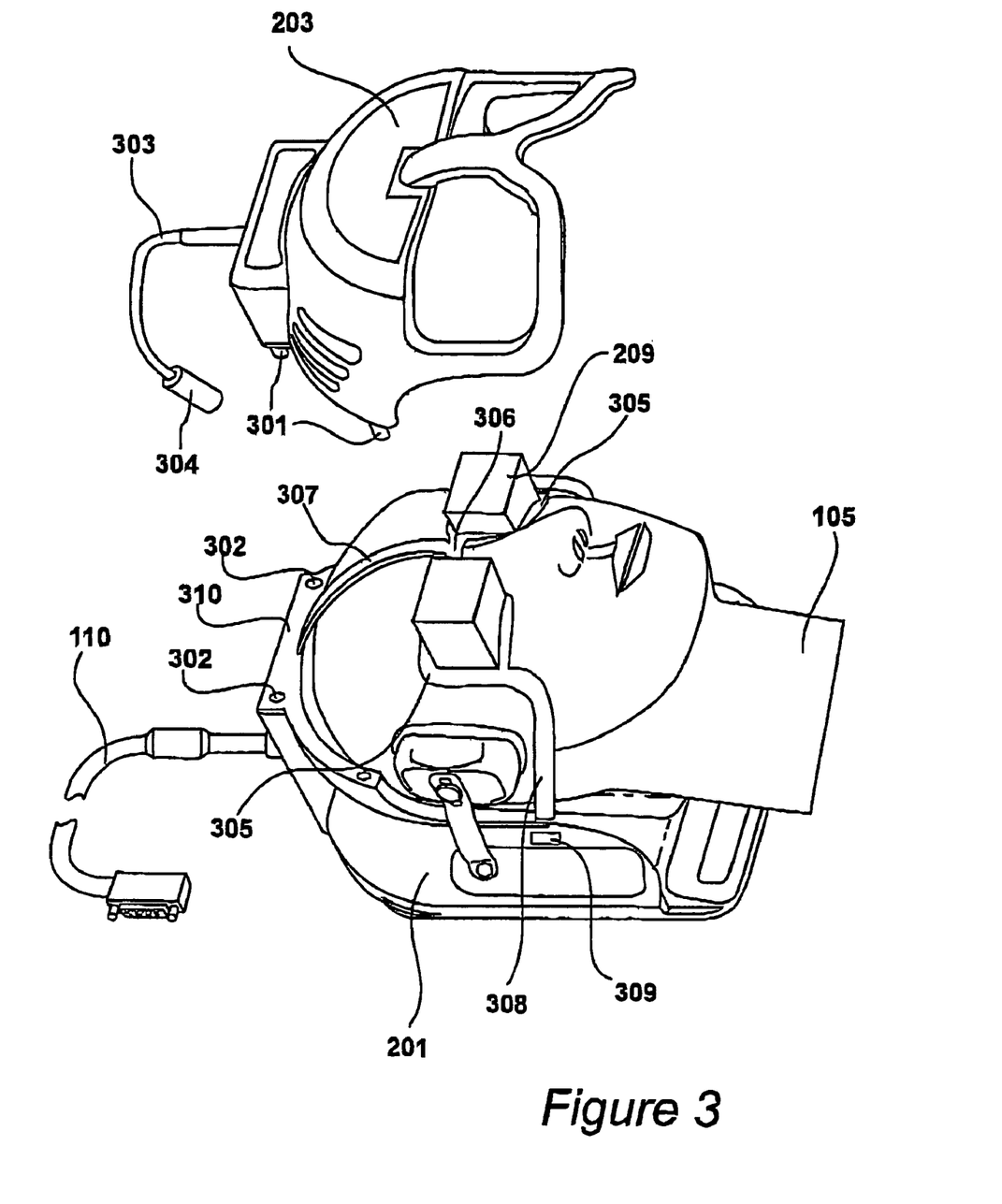
FIG. 3 shows the receiving coil apparatus 102 with the upper part 203 removed from the lower part 201.

The receiving coil apparatus 102 is shown in FIG. 3 with the upper part 203 removed from the lower part 201. In order to allow the person to get in and out of the apparatus 102, the upper part 203 is removably connected to the lower part 201 by a series of lugs or connectors 301 and corresponding sockets 302.

The upper part 203 has a preamplifier for each of its coils, and an output lead 303 which caries an output from each preamplifier to a male connector 304. The lower part 201 has a corresponding female connector (not shown) for connecting to connector 304 when the upper and lower parts are brought together. Consequently, during use, signals from the preamplifiers of both the upper and lower parts of apparatus 102 are supplied to the processing device 104 via cable 110.

The goggles 209 are comprised of portions 305 configured to be positioned over a wearer's eyes such that they rest on their cheek bones and lower forehead. To provide a comfortable fit, the portions 305 are provided provide with an MRI compatible soft resilient material, on the side facing the person's face. The portions 305 are connected by a bridge 306 configured to extend across the top of a wearer's nose.

An arm 308, configured to fit down the side of the wearer's face and under their ears, extends from each portion 305. A third arm 307, configured to extend over the wearer's forehead and towards the top of their head, extends from the bridge 306. Each of the three arms (307 and 308) has an end that is configured to be anchored in a socket in the lower part 201 by a ratchet mechanism. The arms (307, 308) are pushed down into the sockets such that the portions 305 press against the face of person 105. The pressure exerted by the goggles 209 against the face of the person 105 resists movement of their head 200.

A button 309 is provided on the lower part 201, for each of the arms (307, 308). When one of the buttons (309) is pressed, the respective ratchet mechanism is released allowing the end of the arm to be withdrawn from the lower part.

In an alternative embodiment, the upper surface 310 of the lower part 201 and lower surface of the upper part 203 are provided with mating electrical connectors that mate as the upper part is located on the lower part.

FIG. 4

Figure 4:
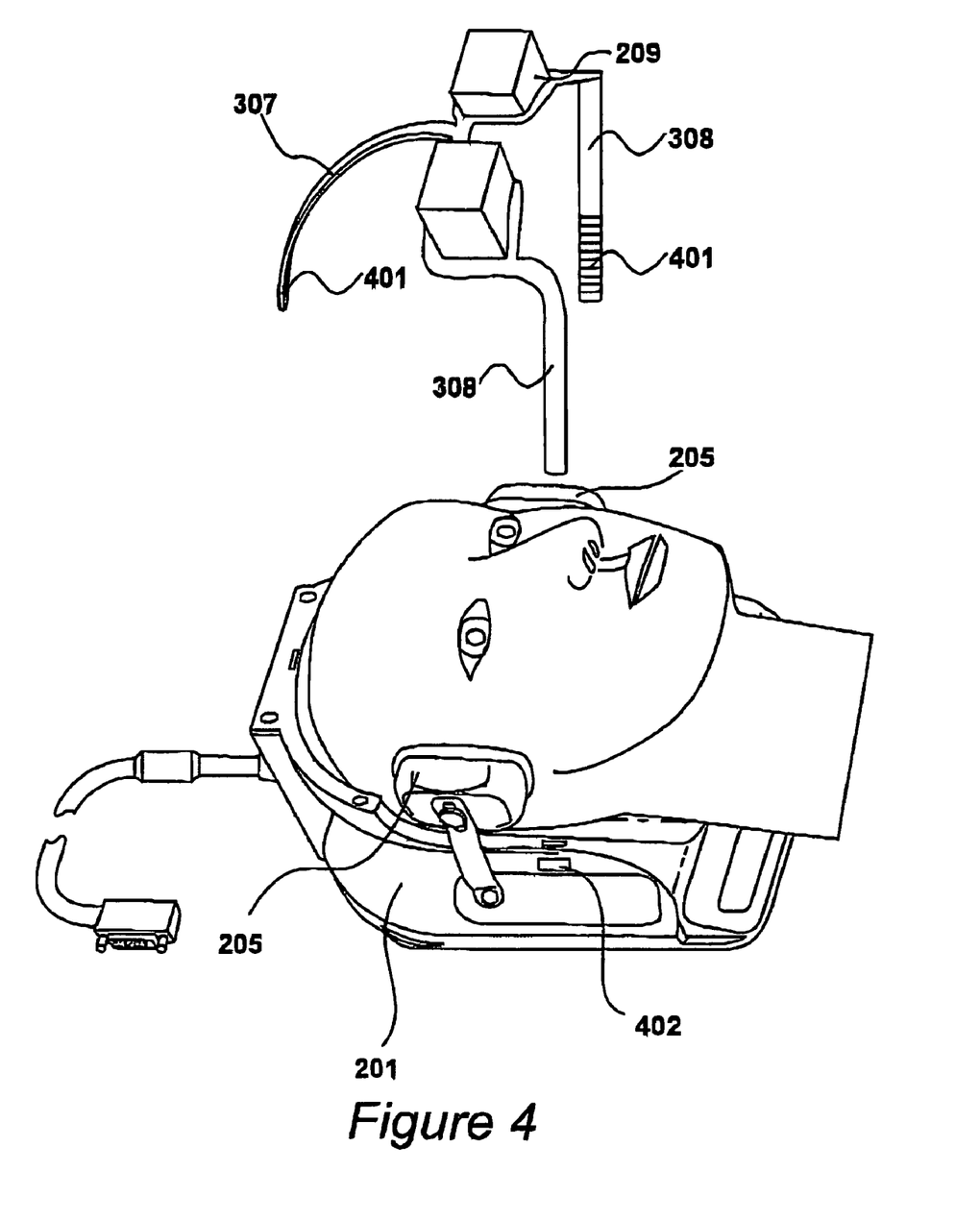
FIG. 4 shows the lower part 201 of the receiving coil apparatus 102 with the goggles 209 separated from the lower part.

The lower part 201 of the receiving coil apparatus 102 is shown in FIG. 4, with the goggles 209 separated from the lower part. A section of the arms 307, 308 of the goggles, nearest to their free end, has a serrated surface 401 configured to engage with a ratchet mechanism located within a respective socket 402 of the lower part 201.

From the above, it will now be understood how the apparatus provides several mechanisms for maintaining the position of a person's head during scanning, and also how the apparatus may be disassembled to allow the person to free themselves from the apparatus.

It should also be understood that, when a person's head is to be scanned, their head is positioned on a shaped cushion within the lower part 201, the earphones 205 are positioned over their ears, the goggles are placed over their eyes while the arms of the goggles are inserted in sockets 402 in the lower part 201, and then the upper part 203 is replaced and electrically connected to the lower part 201.

In an alternative arrangement, the upper and lower parts of the apparatus are provided with a sliding mechanism, whereby the upper part slides backwards away from the lower part to allow the person to be released. In this embodiment, mirrors may be mounted onto the upper part itself, in place of goggles.

FIG. 5

Figure 5:
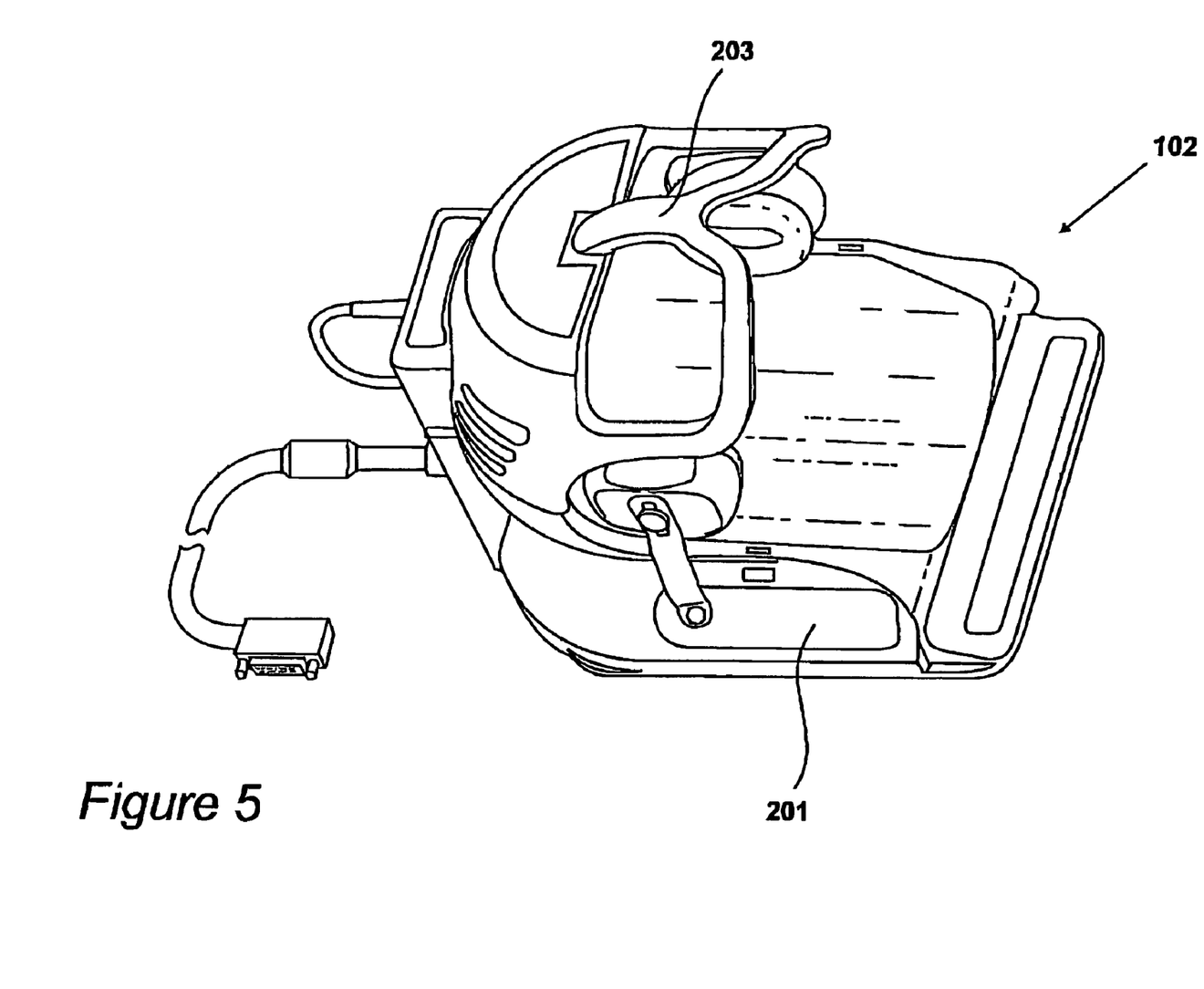
FIG. 5 shows the receiving coil apparatus 102 without the goggles 209, but with the upper part 203 replaced on the lower part 201.

The receiving coil apparatus 102 is shown in FIG. 5, without the goggles 209, but with the upper part 203 replaced on the lower part 201.

An alternative receiving coil apparatus, similar to apparatus 102 does not make use of goggles that are used to stabilize the head. If goggles are required, they may be worn within the apparatus, or adjustably attached to a part of the upper part of the apparatus adjacent the eyes of the person to be scanned.

FIG. 6

Figure 6:
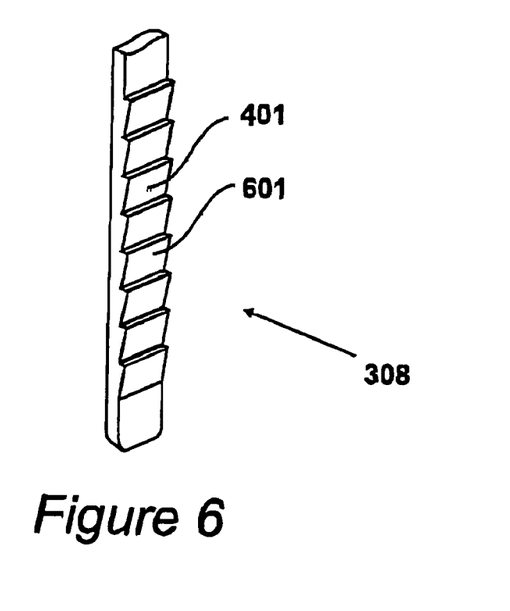
FIG. 6 shows in detail the free end of a goggles arm 308.

The free end of a goggles arm 308 is shown in detail in FIG. 6. The serrated face 401 comprises several, in this example eight, saw-tooth shaped teeth, such as the tooth 601. By having several teeth the arm is provided with a means for adjusting the position of the goggles with respect to the base, to allow a variety of sizes of head to be accommodated.

FIG. 7A

Figure 7A:
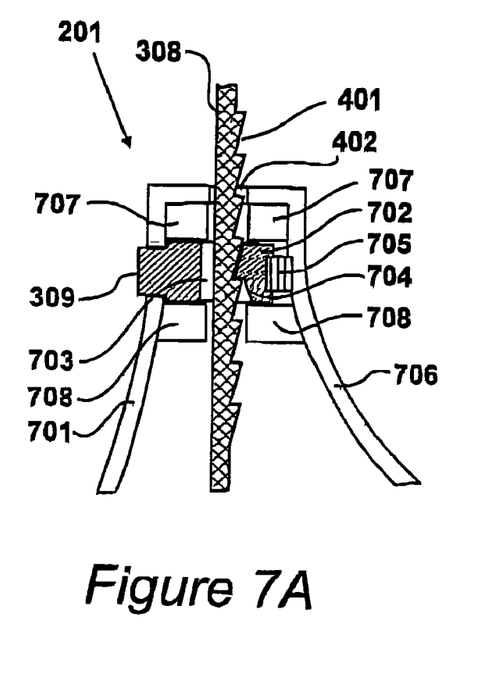
FIG. 7A shows a cross sectional view the arm 308 restrained within a socket 402 of the lower part 201.

The arm 308 restrained within a socket 402 is shown in the cross sectional view of FIG. 7A. The button 309 extends through the outer wall 701 of the lower part 201, and it forms part of a locking member 702. The locking member 702 has a rectangular aperture 703 which has three smooth surfaces and a serrated surface 704. The serrated surface 704 of the locking member is configured to lock against the serrated surface 401 of the arm 308. A resilient member, in the present example in the form of a compression spring, is located between the locking member and the upper wall 706 of the lower part 201. The resilient member 705 is configured to apply a force to the locking member 702 to maintain it in the locked position shown in FIG. 7A. The locking member 702 is located between upper guides 707 and lower guides 708 such that it can slide between the guides when the button 309 is pressed.

FIG. 7B

Figure 7B:
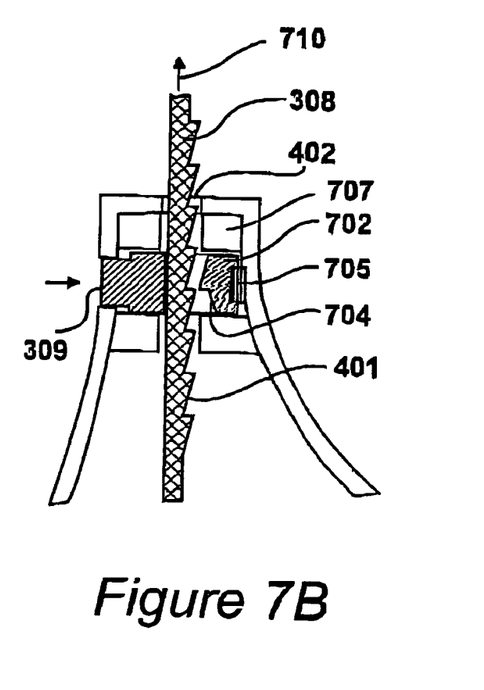
FIG. 7B shows the arrangement of FIG. 7A after the button 309 has been pressed to release the arm 308.

The arrangement shown in FIG. 7A is shown in FIG. 7B after the button 309 has been pressed. Upon pressing the button 309 the locking member 702 compresses the resilient member 705, and consequently the serrated surface 704 of the locking member is moved away from the serrated surface 401 of the arm. Thus, the surfaces 401 and 704 are no longer interlocked and the arm 308 may be withdrawn from the socket in direction of arrow 710.

When the arm 308 is re-inserted into the socket 402, the guides 707 provide a guide for the arm so that it passes through the aperture in locking member 702, and the resilient member 705 compresses sufficiently to allow the serrated surface 704 of the locking member to ride over the serrated surface 401 of the arm. Thus, the arm can be pushed into the socket 402 until sufficient pressure is applied by the goggles to the persons face, and then the locking member automatically locks the arm in place.

FIG. 8

Figure 8:
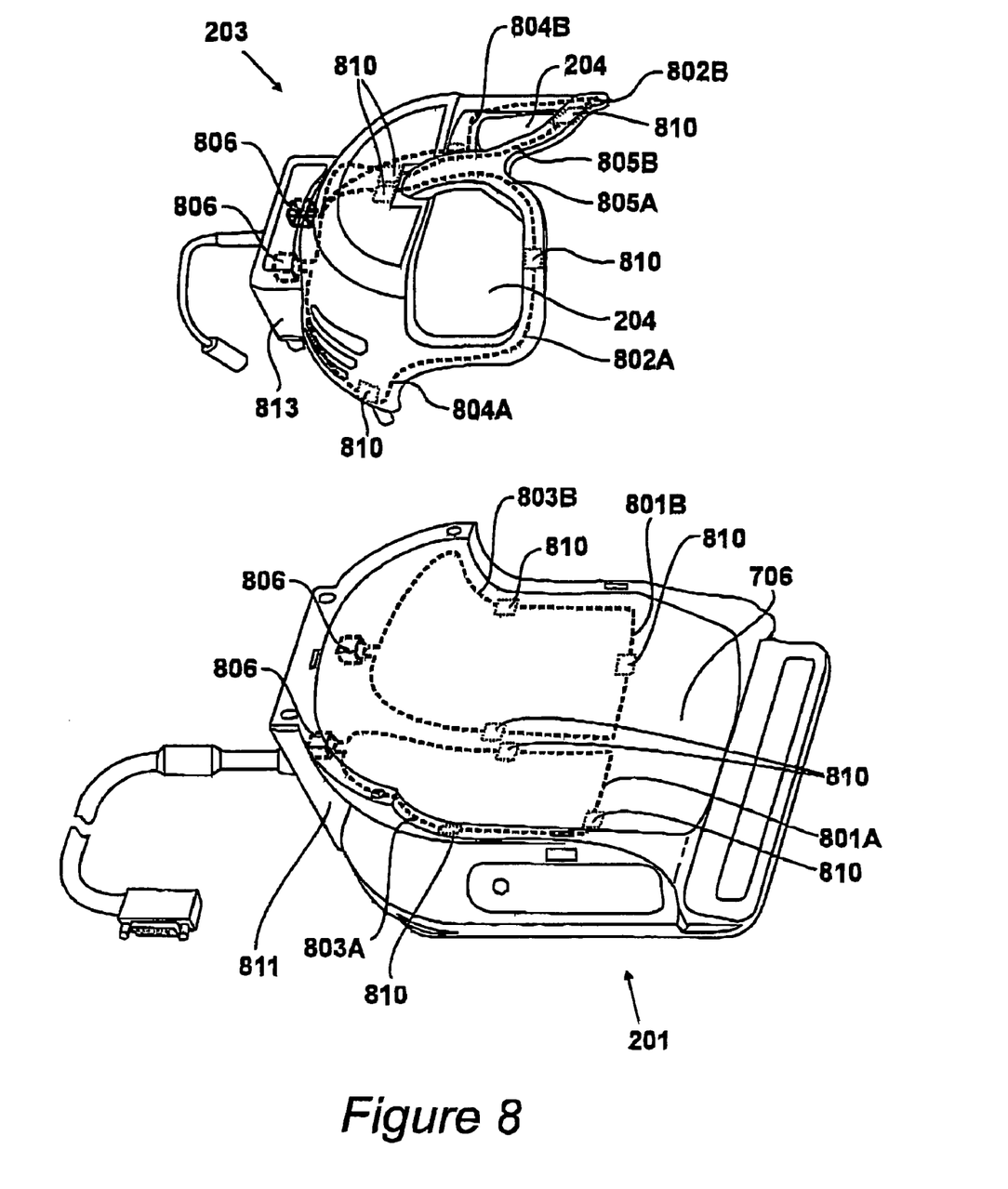
FIG. 8 shows the position and shape of the RF receiving coils of apparatus 102.

The position and shape of the RF receiving coils of apparatus 102 is shown in FIG. 8. The earphones and goggles have been removed for the purposes of clarity. The upper part 203 and lower part 201 of apparatus 102 are each provided with a pair of RF receiving coils. The lower part 201 has coils 801A and 801B, while the upper part 203 has coils 802A and 802B. Each of the coils has an irregular shape to closely contour the head, to conform to the earphone cut outs and allow clearance for the nose and eyes. The coils have a spatial sensitivity distribution that will generate signals suitable for parallel imaging.

The coils 801A and 801B are mounted to the underside of the upper wall 706 of the lower part 201, each of said coils being a mirror image of the other and arranged symmetrically in the lower part 201. Coil 801B is arranged to extend around the rear left half of a person's head and has a portion 803B having an outer boundary configured to curve around the back and top of the persons left ear. Coil 801A is similarly configured to extend around the rear right half of a person's head and has a portion 803A having an outer boundary configured to curve around the back and top of the person's right ear.

In a similar manner, the coils 802A and 802B are mounted within the upper part 201, each of said coils being a mirror image of the other and arranged symmetrically in the upper part. Coil 802A has an outer boundary configured to extend around the front right half of a person's head, and has a portion 804A configured to curve up around the front and top of a person's right ear. In addition, the outer boundary of coil 802A has a portion 805A that is configured to follow a contour between a person's eyes, around the bridge of their nose and below their right eye. Likewise, coil 802B has an outer boundary configured to extend around the front left half of a person's head, and has a portion 804B configured to curve up around the front and top of a person's left ear. In addition, the outer boundary of coil 802B has a portion 805B configured to follow the contour between a person's eyes, around the bridge of their nose and below their left eye.

Each of the coils 802A and 802B is arranged to extend down to a level below a person's eyes, and around a respective one of the two apertures 204.

Although coils 801A and 801B are a different shape to 802A and 802B, all four coils are arranged to surround substantially the same area. It should also be noted that each coil defines an area which extends around only a portion of the circumference of the head, but taken together, the areas defined by all four coils form a band which extends completely around the head.

The lower part 201 and upper part 203 each have a respective rear compartment 811 and 813 which houses electronic circuits 806 of the coils. (The electronic circuits 806 are described below in detail with reference to FIG. 10.)

Each of the four coils 801A and 801B, 802A and 802B is comprised of a single loop having four segments connected by a de-coupling circuit 810 arranged to be approximately equally spaced around the loop. These circuits de-tune the loop to ensure the loop does not couple with the transmit RF coil during the RF pulse. In any specific embodiment the number of de-tuning circuits is chosen to ensure that the coil is properly de-coupled from the transmit coil during the RF pulse. Thus, in alternative embodiments each coil may have two or four de-coupling circuits.

FIG. 9

Figure 9:
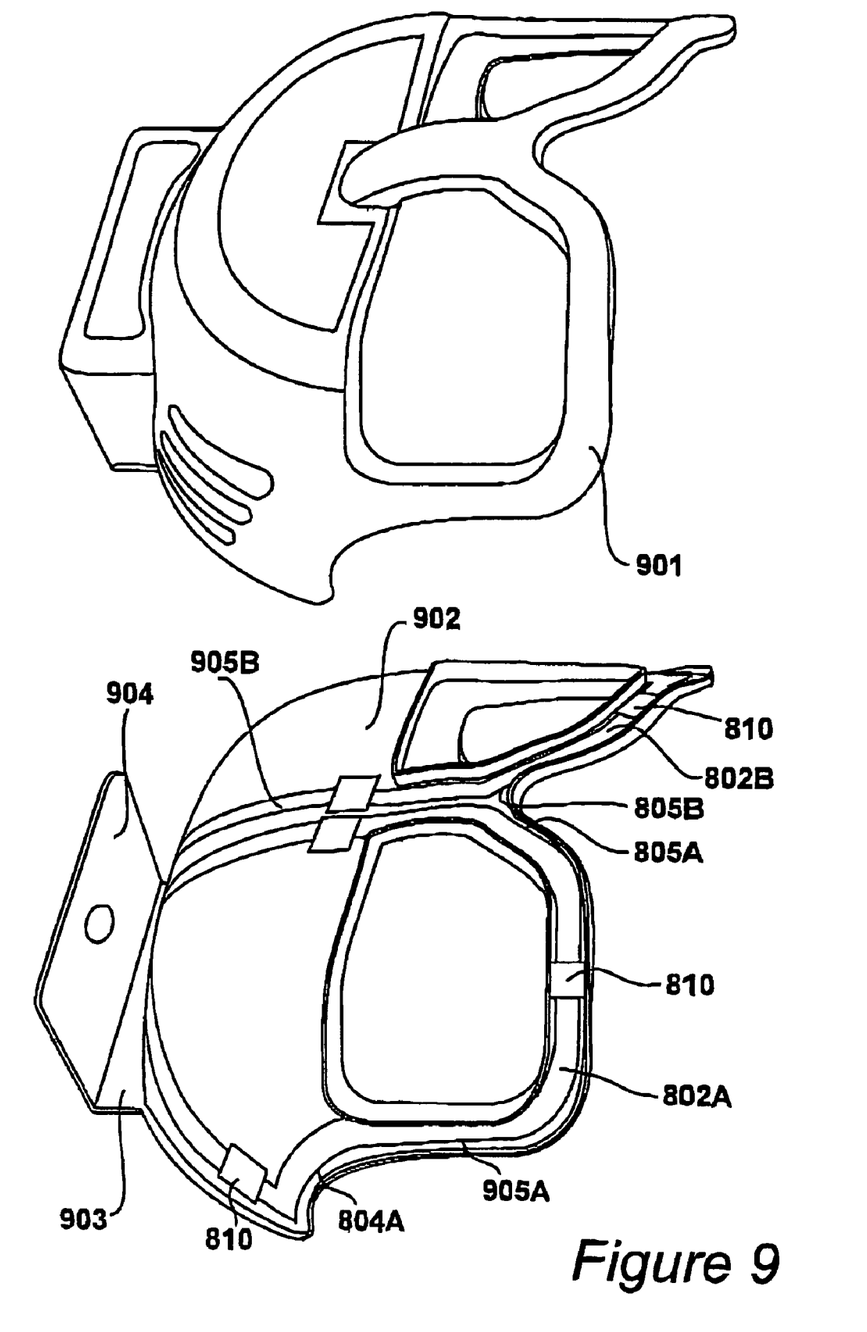
FIG. 9 illustrates the construction of the upper part 203.

The construction of the Lipper part 203 is illustrated in FIG. 9. The upper part 203 is comprised of an outer shell 901 and an inner shell 902, each shell being of a molded plastic construction. The shells may be configured to be fixed together by bonding, clipping, screwing or any other suitable method.

The coils 802A and 802B are comprised of pieces of copper coated polymer sheet cut to the required shape and bonded to the inner shell. Alternatively, copper foil is used in place of the copper coated polymer sheet. The de-coupling circuits 810 may be similarly bonded to the inner shell.

The inner shell 902 is contoured to closely fit over the front of a person's head. Therefore, it has a concave inner surface such that in use it curves circumferentially around a person's head from the middle of the forehead towards the sides of the head and also curves longitudinally around from the forehead towards the top of the head. Consequently, the coils 802A and 802B lay on a similar concave surface to provide close spacing between themselves and a person's head.

The coils 801A and 801B in the lower part 201 are similarly constructed and mounted to the underside of its upper wall 706. Pus to the concave upper surface 202, the lower coils 801A and 801B are located on a concave surface which in use curves circumferentially around the of person's head from the back towards the sides of the head and also curves longitudinally around from the back of the head towards the top of the head.

The inner shell 902 also forms the lower wall 903 and rear wall 904 of the compartment 813 in which the upper electronic circuits 806 (not shown in FIG. 9) are located.

As shown in FIG. 9, the coils 802A and 802B have an outer boundary 905A and 905B respectively which is shaped along the portions 805A and 805B to follow the contour around the nose of a person. Because of this shaping it has been possible to design the inner shell such that, in use, a close spacing is provided between the coils and a person's face adjacent their nose.

Similarly, the shape of the outer boundary 905A at portion 804A allows the shell to fit around an ear and allows close spacing between the coil and the head adjacent the ear.

The close spacing facilitated by the shaping of the coils around the nose and ears provides the RF receiving coil apparatus 102 with improved signal to noise ratios when compared to conventional apparatus.

FIG. 10

Figure 10:
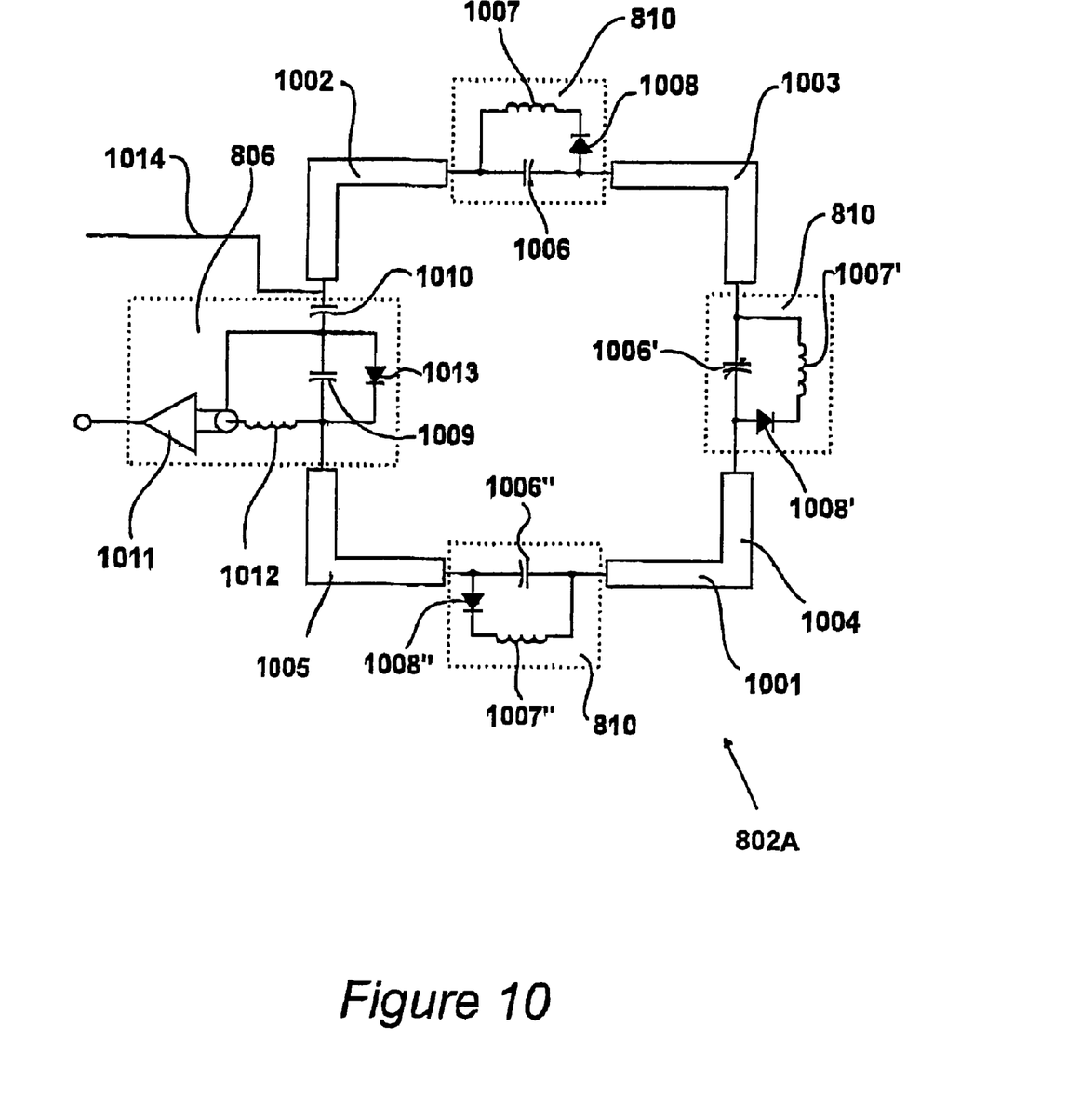
FIG. 10 shows schematically the electrical configuration of RF receiving coil 802A.

The RF receiving coil 802A, is shown schematically in FIG. 10. It should be noted that each of the RF receiving coils 801A, 801B, 802A and 802B are similarly electrically configured.

RF coil 802A comprises a single loop of copper 1001 comprising four segments 1002, 1003, 1004 and 1005. Three de-coupling circuits 810 connect adjacent pairs of the segments and the loop is closed by the electronic circuit 806.

Each de-coupling circuit 810 is similarly configured and comprises a capacitor 1005, 1006', 1006" in series with the loop segments 1002, 1003, 1004 and 1005, and an inductor 1007, 1007', 1007" in series with a PIN diode 1008, 1008', 1008", such that the inductor and diode are connected in parallel with a respective one of said capacitors.

The electronic circuit 806 comprises: a pair of capacitors 1009 and 1010 connected in series with the loop segments 1002 to 1005; a low impedance preamplifier 1011 which has a first input connected to one side of capacitor 1009, and a second input connected to the other side via an inductor 1012; and a PIN diode 1013 connected in parallel with the capacitor 1009.

The outputs of each of the pre-amplifiers 1011 of each electronic circuit 806 are provided as outputs from the apparatus 102, for supply to processing equipment, such as equipment 104.

The PIN diode 1008, 1008', 1008" in each decoupling circuit 810 is actively switched under control from the scanner control unit through a signal input 1014 so that current cannot flow through the respective inductor 1007, 1007', 1007" in a receive mode, but current is able to flow during a transmit mode while the transmitting coils are transmitting. The value of the capacitors 1006, 1006' and 1006", and 1009 and 1010 are selected such that during the receive mode when the inductors 1007, 1007', 1007" are effectively open circuit, the RF receiving coil 802A is tuned to the center frequency of the MR scanner.

The value of the inductors 1007, 1007', 1007" are chosen such that with the respective capacitor 1006, 1006', 1006" they form resonant circuits which resonate at the center frequency of the scanner. As a result, during the transmit mode, the resonating circuits add high impedance to the RF coil loop causing it to be de-tuned. Consequently, signal applied to the preamplifier is reduced. In addition, the PIN diode 1013 is configured to conduct during transmission, thus shorting out the capacitor 1009 and further reducing RF transfer to the preamplifier.

The capacitor 1009 and inductor 1012 of the electronic circuit 806 are chosen so that their resonant frequency is the same as the scanner frequency. Thus, they provide a quarter wavelength impedance conversion at the operating frequency, whereby said inductor and capacitor provide a matching circuit across the low impedance preamplifier 1011 that converts the low impedance at the preamplifier to a high impedance across the coil. Consequently, the receive coil 802A and similarly the other receive coils (801A, 801B, 802B) in the apparatus, have a high impedance and do not couple with one another. Thus, they are able to operate without interference from neighboring coils.

FIG. 11

Figure 11:
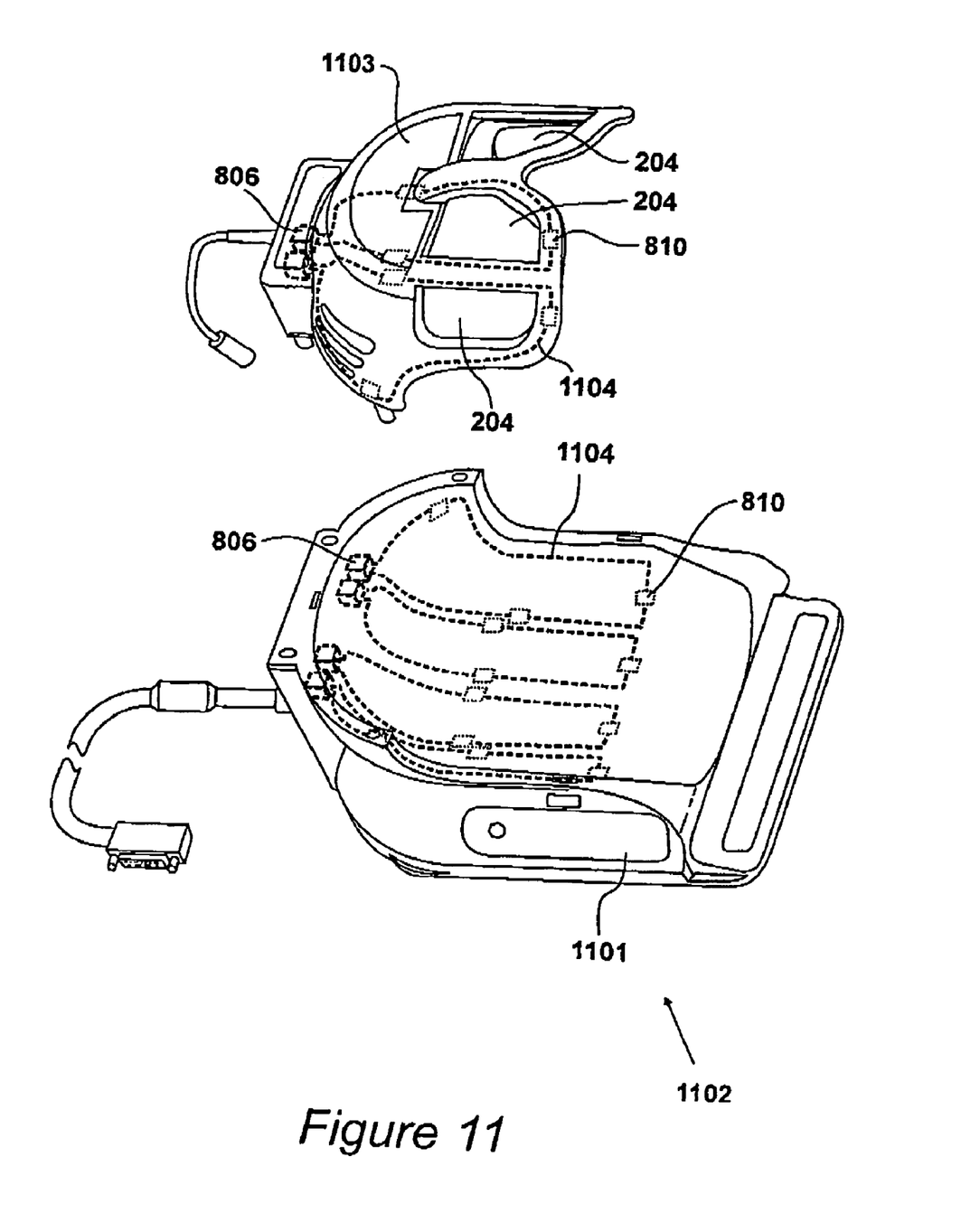
FIG. 11 shows an alternative RF receiving coil apparatus 1102.

An alternative RF receiving coil apparatus 1102 is shown in FIG. 11. This apparatus is provided with earphones and goggles in the manner of apparatus 102 but these are not shown in FIG. 11. The apparatus 1102 has a similar structure to apparatus 102, having a lower part, or base, 1101 and an upper part 1103. However, apparatus 1102 differs from apparatus 102 in that it has eight RF receiving coils instead of four; the lower part 1101 and the upper part 1103 each being provided with four coils 1104. For clarity, only the two coils in the right half of the upper part 1103 are shown, but it should be understood that the left half also has two similar coils.

Like apparatus 102 each coil is provided with de-coupling circuits 810 spaced around the coil and electronic circuitry 806 including a low impedance preamplifier.

The inner and outer shell of the upper part 1103 include an additional element which bridges the apertures 204, allowing segments of each of the upper coils to be supported.

FIG. 12

Figure 12:
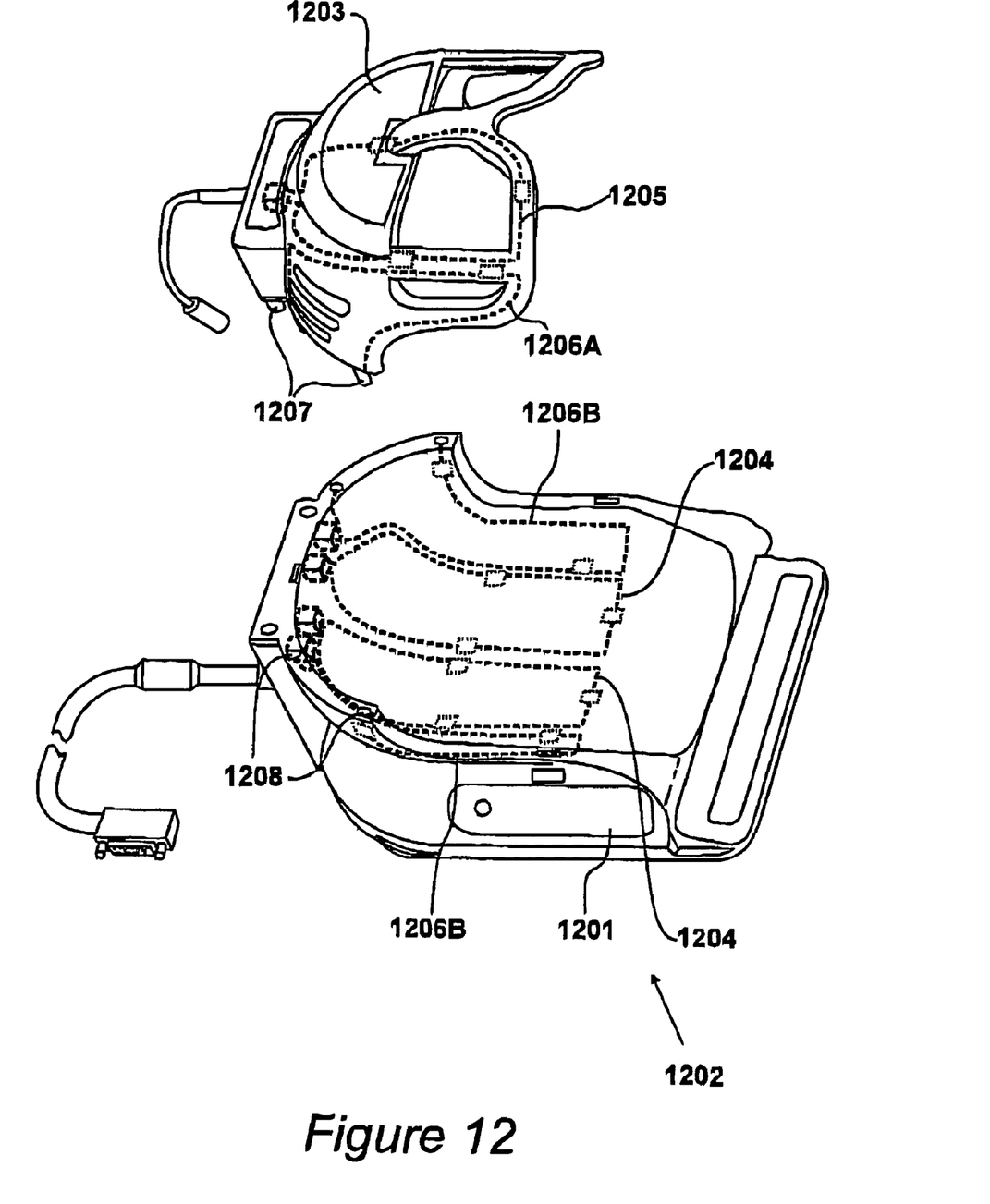
FIG. 12 shows a further alternative RF receiving coil apparatus 1202.

A further alternative RF receiving coil apparatus 1202 is shown in FIG. 12. This apparatus is provided with earphones and goggles in the manner of apparatus 102 but these are not shown in FIG. 12. The apparatus 1202 has a similar structure to apparatus 102, having a lower part, or base, 1201 and an upper part 1203. However apparatus 1202 differs from apparatus 102 in that it has six RF receiving coils instead of four. Two coils 1204 of the six are located wholly within the lower part 1201, two coils 1205 are located wholly within the upper part 1203 and two split coils have portions 1206A in the upper part 1203 and portions 1206B in the lower part 1201. (For purposes of clarity only one of the two coils 1205, and only one of the two portions 1206A, is indicated in FIG. 12. However, the coil configuration within the apparatus 1202 is symmetrical.)

In the present embodiment some of the lugs and sockets that provide a means of connection between the upper and lower parts also provide a means of electrical connection between coil portions 1206A and 1206B. Thus, for example, the upper coil portion 1205A is connected at each end to a conductive pin 1207, and each end of the lower coil portion 1206B is electrically connected to conductive elements within sockets 1208. The conductive elements of sockets 1208 are configured to make electrical contact with the pins 1208 when they are inserted and thereby form a complete coil.

In a further alternative embodiment (not shown) a similar RF receiving coil apparatus has six coils, each surrounding similar areas, and four coils are housed in the lower part and two in the upper half. To accommodate the additional coils, the lower part extends further to cover the lower section of the head, when compared to previous embodiments, and the upper part is made smaller. Consequently, the separation of the two parts is arranged to be just in front of a person's ears, and only the lower part of the apparatus contains coils having an outer boundary that is configured to extend around an ear of a head when positioned in the apparatus.

It should be understood that the number of coils in an array may be varied from the four, six, or eight coils of the embodiments in the above description.

The invention claimed is:

1. Magnetic resonance scanning apparatus for imaging parts of a human head of a person comprising:

a plurality of RF coils configured to receive an RF signal including a lower pair of RF coils and an upper pair of RF coils;

a lower part; and an upper part, wherein said lower part has an upper wall configured to provide support for the back of the human head, said lower pair of RF coils is rigidly mounted within the lower part adjacent the upper wall, said upper part has a rigid structure supporting said upper pair of RF coils, each of said RF coils are located on a concave surface configured to curve circumferentially around the human head and curve longitudinally around the human head when located within the apparatus, each of said upper pair of RF coils has an outer boundary configured to follow a contour between the eyes, around the bridge of a nose and below a respective eye of the human head when located within the apparatus to allow the nose to extend between said upper pair of RF coils, whereby a close spacing is facilitated between the RF coils and an upper part of the human head including a part which is adjacent to the eyes, and said apparatus further comprises goggles attachable to the lower part and configured to press directly on the face of the person to resist the movement of their head.

2. Magnetic resonance scanning apparatus according to claim 1, wherein the upper part defines a pair of apertures such that each said aperture is surrounded by one of said upper RF coils such that when the human head is located within the apparatus the eyes are able to see out from the apparatus.

3. Magnetic resonance scanning apparatus according to claim 1, wherein at least one of said plurality of RF coils has a curved outer boundary configured to extend partly around an ear of the human head when positioned within the apparatus, to facilitate a closely spaced relationship between said RF coil and the head.

4. Magnetic resonance scanning apparatus according to claim 1, wherein each of the lower pair of RF coils has a curved outer boundary configured to extend partly around an ear of the human head when positioned within the apparatus, to facilitate a closely spaced relationship between said lower pair of RF coils and the head.

5. Magnetic resonance scanning apparatus according to claim 4, wherein each of the upper pair of RF coils has a curved outer boundary configured to extend partly around a respective ear of the human head when positioned within the apparatus, to facilitate a closely spaced relationship between said upper pair of RF coils and the head.

6. Magnetic resonance scanning apparatus according to claim 1, wherein the lower part contains more RF coils than the upper part.

7. Magnetic resonance scanning apparatus according to claim 1, wherein each of the RF coils are configured to provide a non-uniform radio frequency field such that said RF coils are useable in a parallel imaging system.

8. Magnetic resonance scanning apparatus according to claim 1, wherein each of said plurality of RF coils is configured to be de-coupled from the other RF coils such that said RF coils are useable in a parallel imaging system.

9. Magnetic resonance scanning apparatus according to claim 8, wherein each of said coils include two or more de-coupling circuits.

10. Magnetic resonance scanning apparatus according to claim 1, wherein the apparatus has a mechanism to attach the goggles which allows the goggles to be detached while the person's head is being located within the apparatus or removed from the apparatus.

11. Magnetic resonance scanning apparatus according to claim 1, wherein the apparatus has a mechanism providing adjustment of the goggles to allow the goggles to be fitted to a variety of head sizes.

12. Magnetic resonance scanning apparatus according to claim 1, wherein the apparatus further comprises ear covers attached to the lower part or upper part, said ear covers being configured to provide a force on the sides of the person's head to resist movement of the head.

13. Magnetic resonance scanning apparatus according to claim 12, wherein the ear covers are headphones.

14. Magnetic resonance scanning apparatus according to claim 1, wherein at least one of the RF coils is split such that said RF coil has one portion in the upper part of the apparatus and one part in the lower part of the apparatus.

15. Magnetic resonance scanning apparatus for imaging parts of a human head of a person comprising:
- a rigid supporting structure configured to extend around the human head;
- a plurality of RF coils rigidly mounted on said supporting structure;
- goggles configured to be positioned over the eyes of the human head and configured to be in contact with the human head; and
- a mechanism allowing the goggles to be attached to the rigid supporting structure wherein when attached together a movement of the human head wearing said goggles is resisted.

16. Magnetic resonance scanning apparatus according to claim 15, wherein the apparatus has a mechanism providing position adjustment of the goggles to allow the goggles to be fitted to a variety of head sizes.

17. Magnetic resonance scanning apparatus according to claim 15, wherein said apparatus further comprises:
- ear covers configured to be positioned over the ears of the human head; and
- a mechanism attaching the ear covers to the rigid supporting structure, said mechanism being configured to press the ear covers against the sides of the human head when positioned in the apparatus such that a movement of the human head is resisted.

18. Magnetic resonance scanning apparatus according to claim 15, wherein the apparatus has a mechanism to attach the goggles which allows the goggles to be detached while the person's head is being located within the apparatus.

19. Magnetic resonance scanning apparatus for imaging parts of a human head of a person comprising:
- a rigid supporting structure configured to extend around the human head;
- a plurality of RF coils rigidly mounted on said supporting structure;
- ear covers configured to be positioned over the ears of the human head; and
- a mechanism comprising resilient support brackets attaching the ear covers to the rigid supporting structure, said mechanism being configured to press the ear covers against the sides of the human head when positioned in the apparatus wherein when attached together a movement of the human head is resisted.

20. Magnetic resonance scanning apparatus according to claim 19 wherein:
- the plurality of RF coils comprise an upper pair of RF coils and a lower pair of RF coils; and
- the rigid supporting structure comprises a lower part and an upper part, the mechanism attaching the ear covers to the lower or upper part,
- said lower part has an upper wall configured to provide support for the back of the human head,
- said lower pair of RF coils is rigidly mounted within the lower part adjacent the upper wall,
- said upper part has a rigid structure supporting said upper pair of RF coils,
- each of said RF coils are located on a concave surface configured to curve circumferentially around the human head and curve longitudinally around the human head when located within the apparatus, and
- each of said upper pair of RF coils has an outer boundary configured to follow a contour between the eyes, around the bridge of a nose and below a respective eye of the human head when located within the apparatus to allow the nose to extend between said upper pair of RF coils, whereby a close spacing is facilitated between the RF coils and an upper part of the head including a part which is adjacent to the eyes.

\* \* \* \* \*